United States Patent [19]

Casey, I. et al.

[11] Patent Number: 4,940,460
[45] Date of Patent: Jul. 10, 1990

[54] PATIENT-FILLABLE AND NON-INVASIVE HYPODERMIC INJECTION DEVICE ASSEMBLY

[75] Inventors: James P. Casey, I., Forest Grove; J. Thomas Morrow, Portland, both of Oreg.

[73] Assignee: Bioject, Inc., Portland, Oreg.

[21] Appl. No.: 283,737

[22] Filed: Dec. 12, 1988

Related U.S. Application Data

[63] Continuation-in-part of Ser. No. 64,762, Jun. 19, 1987, Pat. No. 4,790,824.

[51] Int. Cl.$^5$ .............................................. A61M 37/00
[52] U.S. Cl. ..................................... 604/143; 604/131
[58] Field of Search ............... 604/143, 142, 141, 134, 604/131, 130, 218, 68, 69, 70, 187, 71

[56] References Cited

U.S. PATENT DOCUMENTS

| | | |
|---|---|---|
| 2,547,099 | 4/1951 | Smooth . |
| 2,704,543 | 3/1955 | Scherer . |
| 2,737,946 | 3/1956 | Hein, Jr. . |
| 2,764,977 | 10/1956 | Ferguson . |
| 3,688,765 | 9/1972 | Gasaway . |
| 3,695,266 | 10/1972 | Lussier . |
| 3,853,125 | 12/1974 | Clark et al. . |
| 3,945,379 | 3/1976 | Pritz et al. . |
| 3,945,383 | 3/1976 | Bennett et al. . |
| 4,403,989 | 9/1983 | Christensen et al. . |
| 4,596,556 | 6/1986 | Morrow et al. . |
| 4,680,027 | 7/1987 | Parsons et al. . |
| 4,717,384 | 1/1988 | Waldeisen ........................ 604/143 |
| 4,790,824 | 12/1988 | Morrow et al. ................... 604/143 |

FOREIGN PATENT DOCUMENTS 492587 5/1953 Canada .

*Primary Examiner*—John D. Yasko
*Attorney, Agent, or Firm*—Lyon & Lyon

[57] ABSTRACT

The assembly includes an injection device which includes a housing having an ampule-receiving chamber, a gas charge, and means for delivering a predetermined amount of gas to the ampule-receiving chamber. The device includes an injection-counting ring which is received in a groove extending about the housing wherein the ring includes a counting mechanism thereon and is constructed to allow one-way only rotation thereof relative to the housing. The patient-fillable ampule of the invention includes an ampule body having a plunger end and an orifice end, a medication retaining cavity and an elongate plunger which is received in one end of the cavity. An orifice-bearing end cap is fixed to the orifice end of the body. A truncated hypodermic needle is received in the end cap. A removable needle is provided for filling the ampule and allows use of the ampule as a conventional syringe. The ampule is attached to the hypodermic device by means of an ampule sleeve which extends about the ampule body along the length thereof and which cooperates with a retainer collar located on the device.

15 Claims, 2 Drawing Sheets

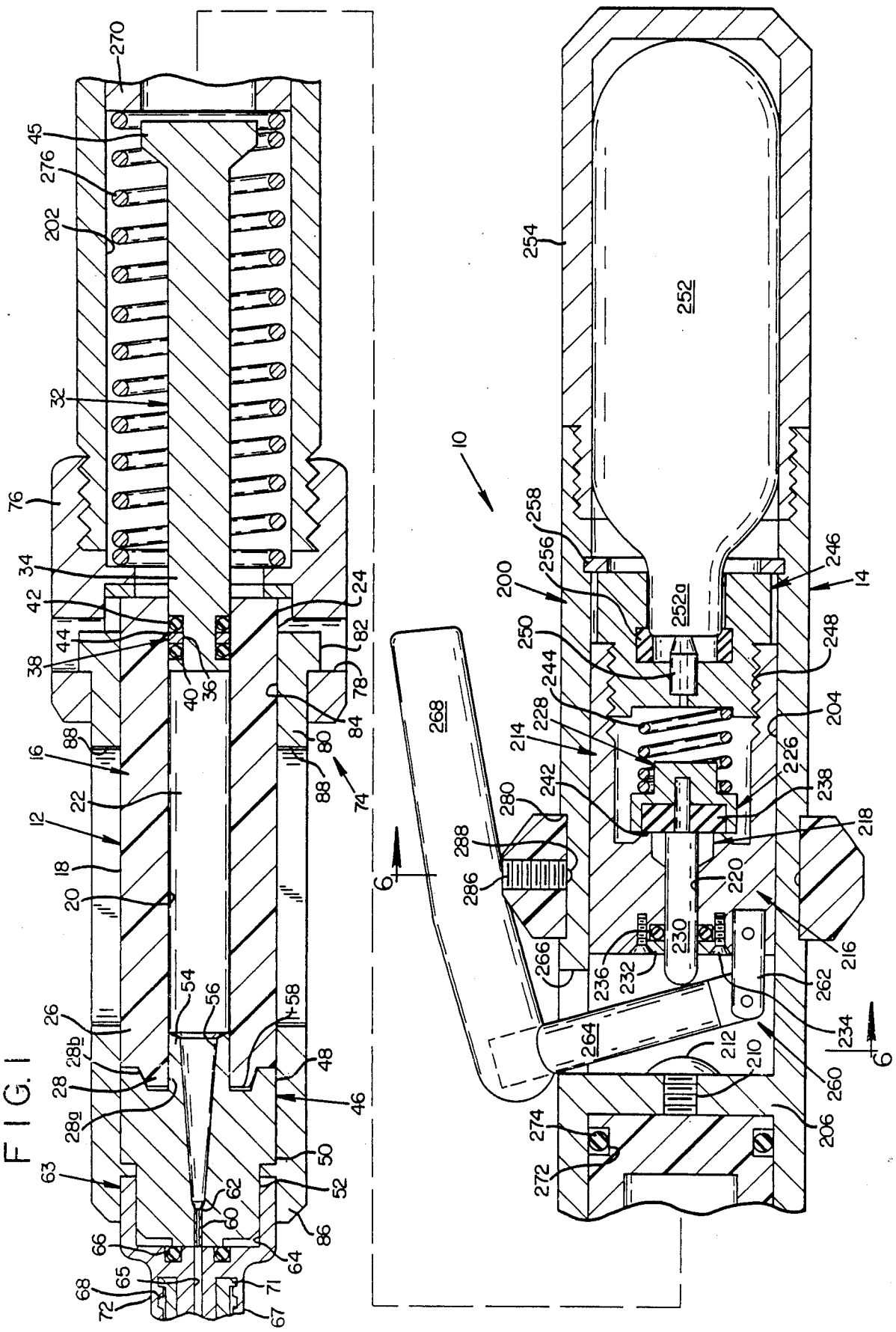

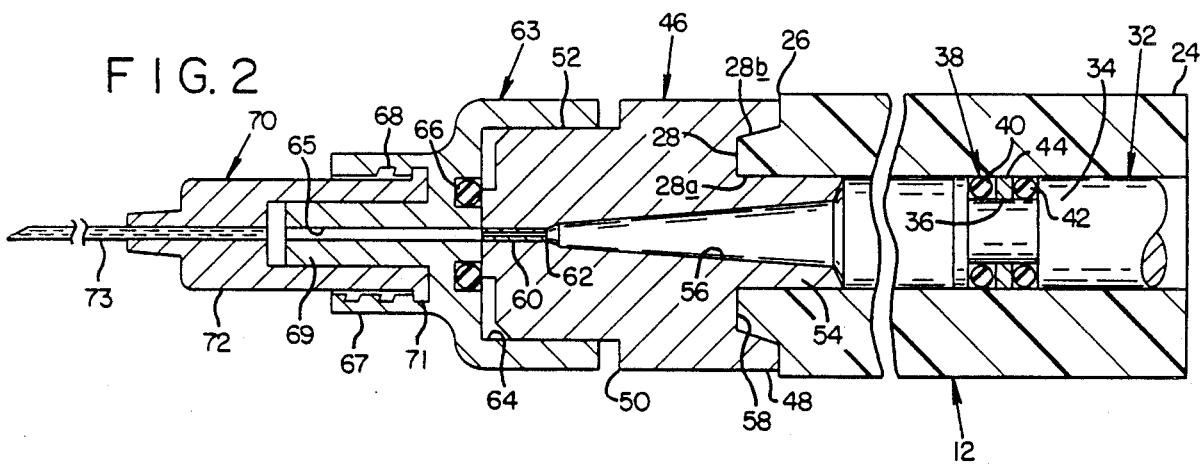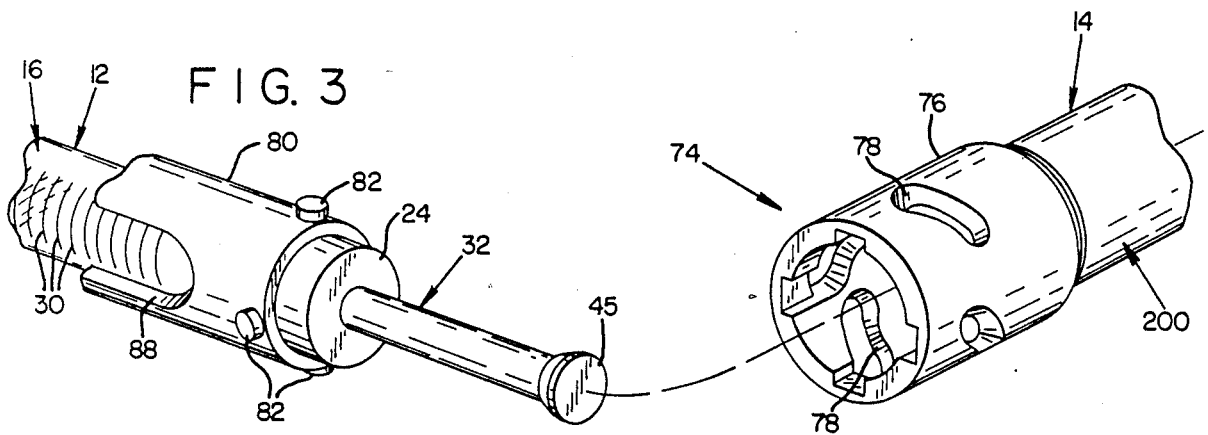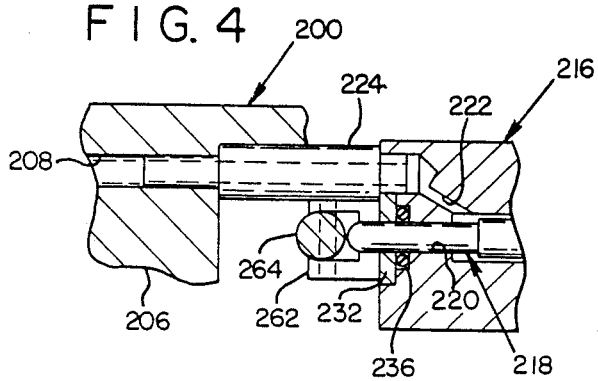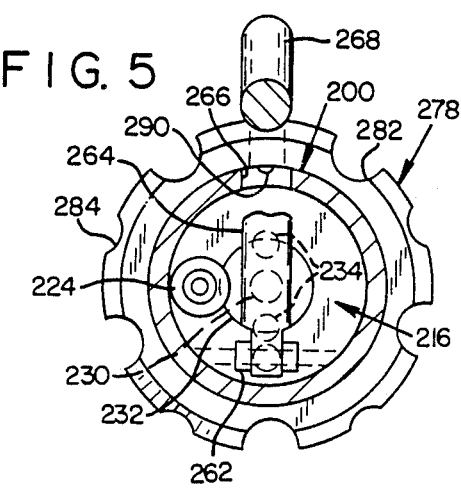

PATIENT-FILLABLE AND NON-INVASIVE HYPODERMIC INJECTION DEVICE ASSEMBLY

This is a continuation-in-part of U.S. patent application Ser. No. 064,762, filed June 19, 1987 for NON-INVASIVE HYPODERMIC INJECTION DEVICE now U.S. Pat. No. 4,790,824. A co-pending application Ser. No. 284,063, filed Dec. 12, 1988 for A PRE-FILLED AMPULE AND NON-INVASIVE HYPODERMIC INJECTION DEVICE ASSEMBLY, describes an ampule which may be filled by a drug manufacturer and thereafter sold and used by a patient providing self-injections. The pre-filled ampule is intended for use with drugs which are potentially unstable or where a precise dosage is required.

BACKGROUND OF THE INVENTION

The invention relates to medication injecting device assemblies and specifically to a patient-fillable ampule for use with a hypodermic injection device which injects medication but which does not require piercing the skin of a patient with a hypodermic needle.

The ampule of the invention described herein is a patient-fillable ampule which may be used by patients with suitable medication wherein the ampule is to be filled by the patient prior to administering the medication. The patient-fillable ampule may be used on a one time only basis or may be used for multiple injections. Additionally, the ampule may be used as a conventional syringe.

Although many forms of syringes are known, the ampule, or syringe of the invention is particularly adapted for use with a powered non-invasive hypodermic injection device wherein the medication is injected through the skin of the patient without the need for piercing the patient's skin with a hypodermic needle. As such, the ampule is subject to extremely high pressures, on the order of 8000 psi, and must therefore be structurally sound to withstand such pressures.

Powered hypodermic devices are known which provide one or multiple gas charges to delivery injection by non-invasive hypodermic means. Generally, the smaller powered hypodermic devices which are intended for use by patient's self-administering medication are one-shot devices, in that a new, gas-filled cartridge must be provided for each injection. Larger devices are known which provide multiple injections from a single gas charge but these devices are generally quite large and too expensive for self-administration of medication. It is particularly important that patients who self-administered medication know how many times the device has been used on a given charge, so that the patient will not attempt to administer medication when the device does not have sufficient gas charge therein to provide a complete injection of the medication.

An object of the invention is to provide a patient-fillable ampule for a powered-hypodermic injection device which will be suitable to withstand the extreme pressures generated by such a device.

Another object of the invention is to provide a powered hypodermic injection device which is capable of providing multiple injections.

A further object of the invention is to provide an ampule for a powered-hypodermic injection device which may be used to provide a non-invasive injection and which may also be used as a conventional, invasive syringe.

Still another object of the invention is to provide such a device which includes means for indicating the number of injections administered on a particular gas charge.

SUMMARY OF THE INVENTION

The assembly of the invention includes an injection device which includes a housing having an ampule-receiving chamber, a gas charge, and means for delivering a predetermined amount of gas to the ampule-receiving chamber. The device includes an injection-counting ring which is received in a groove extending about the housing wherein the ring includes a counting mechanism thereon and is constructed to allow one-way only rotation thereof relative to the housing.

The patient-fillable ampule of the invention includes an ampule body having a plunger end and an orifice end, a medication retaining cavity and an elongate plunger which is received in one end of the cavity. An orifice-bearing end cap is fixed to the orifice end of the body. The end cap has a generally cylindrical form of substantially the same outside diameter of the ampule body along a first length thereof and a stepped-down diameter along a second length thereof. The end cap includes a medication-receiving portion which extends axially from the larger diameter end thereof into the medication retaining cavity. A truncated, conical bore is contained in the medication-receiving portion, with the wider end of the bore located in the medication retaining cavity of the body. A truncated hypodermic needle is received in the end cap at the smaller diameter end thereof and has a channel therein which communicates with the narrow end of the bore in the end cap. The ampule is attached to the hypodermic device by means of an ampule sleeve which extends about the ampule body along the length thereof and which cooperates with a retainer collar located on the device. The ampule is constructed to receive an external fill adaptor on the end cap. The external fill adaptor includes an internal luer lock fitting to join with an industry standard needle for filling the ampule. The needle may also be used to provide an invasive injection using the ampule as a conventional syringe.

These and other objects and advantages of the invention will become more fully apparent as the description which follows is read in conjunction with the drawings.

BRIEF DESCRIPTION OF THE DRAWINGS

FIG. 1 is a medial section of the invention, with the ampule depicted in a ready condition.

FIG. 2 is a greatly enlarged, partial medial section of the ampule of FIG. 1.

FIG. 3 is an exploded perspective view of attachment means of the invention.

FIG. 4 is an enlarged section of an actuator mechanism of the invention.

FIG. 5 is a cross section of one end of a valve assembly of the invention, taken generally along the line 6—6 of FIG. 1.

DETAILED DESCRIPTION OF THE PREFERRED EMBODIMENTS

Referring now to the drawings, and initially to FIG. 1, an ampule and a non-invasive hypodermic injection device assembly constructed according to the invention is shown generally at 10. Assembly 10 includes a patient-fillable ampule, indicated generally at 12 and a powered hypodermic injection device, indicated generally at 14.

Now referring to FIGS. 1 and 2, ampule 12 includes an ampule body 16 which, in the preferred embodiment, is formed of a polycarbonate material. The body has a generally, elongate cylindrical form with an outer wall 18 having a predetermined diameter and an inner wall 20 having a second, lesser predetermined diameter. Inner wall 20 defines a medication retaining cavity 22. Body 16 has a plunger end 24 and an orifice end 26. A flange 28 is located on plunger end 24 and has an inner wall 28a, which is a continuation of body inner wall 20, and an outer wall 28b, which is located intermediate the body inner wall and the body outer wall, and which has a inwardly sloped orientation. The ampule body has, and now referring briefly to FIG. 4, medication-volume indicia 30 located on the outer wall thereof to indicate the amount of medication which is contained in the ampule when the ampule has been filled.

Returning now to FIGS. 1 and 2, ampule 12 includes an elongate plunger 32, one end 34 thereof having a seal-carrying groove 36 formed about the periphery thereof. A seal 38 is carried in the groove and is operable, with the plunger one end, to seal one end of the medication retaining cavity 22 in which the plunger and seal is received.

Seal 38 includes a pair of O-rings, 40, 42 which are separated by a backup ring 44. Seal 38 may be constructed as a unitary element having the desired cross section, with the individual components thereof being joined by a thin web. The other end of plunger 32 includes a plunger head 45. In the preferred embodiment, plunger 32 is formed of polycarbonate.

Ampule 12 includes an orifice-bearing end cap 46 which is fixed to orifice end 26 of body 16. In the preferred embodiment, end cap 46 has a generally cylindrical form and is substantially the same, larger, diameter as the predetermined diameter of outer wall 18 along a first length 48 thereof. A stepped region 50 is located between first length 48 and a second length 52 which has a smaller, stepped-down diameter.

A medication-receiving portion 54 extends axially from the first-length area, or one end, of end cap 46 into medication retaining cavity 22. A truncated, conical bore 56 is located in medication-receiving portion 54 and extends into first length 48 of end cap 46. The wider end of bore 56 is located in cavity 22.

A groove 58 extends about the base of medication-receiving portion 54. Groove 58 is conformal with flange 28 on ampule body 16 and is received thereon.

End cap 46 contains a truncated hypodermic needle 60 having a channel 62 extending therethrough. Truncated needle 60 is co-terminal with, or may be slightly recessed from, the exterior, or other, end of end cap 46 such that the needle does not extend beyond the bounds of the end cap. Channel 62 communicates with the smaller end of bore 56, providing a continuous passage from cavity 22 through the end of needle 60. In forming the preferred embodiment of end cap 46, the cap is injection molded into a mold cavity which clamps needle 60 in place, thereby resulting in a completed end cap having the needle integrally formed therewith. End cap 46 is secured to ampule body 16 by adhesive, or by ultrasonic welding.

An external fill adaptor 63 is installed on end cap 46 and includes a receptacle 64, which fits over the second, stepped-down length of end cap 46. Adaptor 63 has a bore 65 extending through the center thereof. Bore 65 is aligned with needle 60 in the end cap. An 0-ring 66 provides a seal between end cap 46 and adaptor 63.

Adaptor 63 is narrowed at the other end thereof opposite receptacle 64 and has an external wall 67 extending about the periphery thereof. Wall 67 includes a set of threads, or grooves, 68 which, in the preferred embodiment, take the form of a luer lock receptacle, or other conventional means.

A central post 69 extends through the interior of external wall 67 and surrounds bore 65. Post 69 is sized to receive a conventional hypodermic needle 70 thereon. Hypodermic needle assembly 70, also referred to herein as a filling needle, includes connection means 71 which cooperate with grooves 68, also referred to herein as means cooperating with connecting means, to secure the filling needle to adaptor 63. Needle 70 includes a needle carrier 72 and a conventional hypodermic needle 73 thereon. Grooves 68 and post 69 are sized to accept any variety or sizes of conventional hypodermic needles which are secured with a luer lock fitting. This enables the user to select an appropriate needle in the event that the ampule is being used as a conventional syringe, and enables the selection of an appropriate needle to pierce the cover on a dispensing medication bottle to draw medication into cavity 22.

Referring now to FIGS. 1 and 3, attachment means for attaching ampule 12 to device 14 are shown generally at 74. In the preferred embodiment, attachment means includes a retaining collar 76 which is secured to device 14. Retaining collar 76 is secured to device 14 in the preferred embodiment by means of threads on the device and on the collar. Collar 76 also has lug-receiving grooves 78 formed thereon.

Attachment means also includes an elongate ampule sleeve 80 which extends about the ampule body along the length thereof and which has a series of lugs 82 arranged about the periphery of one end 84 thereof. The lug-containing end of the sleeve is located adjacent the plunger end 24 of the ampule body. The other end of the sleeve extends beyond orifice end 26 of the ampule body and encapsulates end cap 46. Sleeve 80 is operable to provide additional retentive force of end cap 46 on ampule body 16 when the medication therein is dispensed under high pressure.

In the preferred embodiment, sleeve 80 has a pair of wasted areas 88 located along the length thereof and provides a view of the contents of the ampule and medication-volume indicia 30 therethrough. Sleeve 80 and end cap 46 comprise what is referred to herein as an ampule shroud.

To prepare the ampule for use, adaptor 63 carrying needle assembly 70 is installed on end cap 46. The plunger is positioned to be completely received in the ampule and needle 73 inserted into a medication-containing bottle. The plunger is then withdrawn partially from cavity 22, drawing medication into the cavity. Once the desired amount of medication has been drawn, as indicated by indicia 30, needle 73 is removed from the dispensing bottle.

In the event that the ampule is going to be used with a powered-injection device, needle assembly 70 and adaptor 63 are removed and the ampule is installed in device 14 as will be described.

If, however, the powered device is not to be used, the user may still conventionally inject the medication using needle assembly 70 and adaptor 63. In this instance, once the ampule is filled with the desired amount of medication, the user simply injects the medication using needle 73 to pierce the skin and depresses the plunger to deliver the medication into their body. The situation may arise in the event that a user does not have an adequately powered cartridge to operate the device or, if for some other reason the user does not desire to use the device for a particular injection. The advantage of the ampule described herein is that the user of a powered injection device does not need to purchase separate ampules or syringes for use with the device, which amplues or syringes may not be used to provide a conventional injection.

In the case where the injection is given non-invasively, the ampule, adaptor and filling needle assembly may be reused. Sterilization will enable reuse of the ampule for the same, or different, medication and for use by the same, or another, person.

Referring now to FIGS. 1 and 3-5, device 14 will be described in greater detail. Device 14 includes a housing 200 which is an elongate, substantially hollow structure having an ampule-receiving chamber 202 at one end thereof and a pressure chamber 204 at the other end thereof. A partition 206 is located between the chambers and includes a gas-delivery passage 208 and a pressure release passage 210 extending therethrough. Pressure release passage 210 has a screw 212 therein which provides for slow release of pressure in ampule-receiving chamber 202 once the device has been fired. Alternately, screw 212 may have a very small diameter orifice therethrough.

A valve assembly, shown generally at 214, is located in pressure chamber 204. Valve assembly 214 includes a valve body 216 which has a cavity 218 therein. Cavity 218 includes a valve shaft-receiving portion 220 and a gas-passage portion 222. A gas transfer tube 224 extends from gas-passage portion 222 to gas-delivery passage 208, thereby connecting cavity 218 with ampule-receiving chamber 202 and maintaining a desired spacing between partition 206 and valve assembly 214.

A poppet valve 226 includes a valve head 228 and a valve shaft 230. Shaft 230 is received in valve-shaft receiving portion 220 and extends beyond one end of valve body 216 through a valve-end retaining plate 232. Retaining plate 232 is held in place by screws 234. An O-ring 236 is located on shaft 230 and provides a gas-tight seal thereabout.

Valve head 228 has an inner, sealing portion 238 and a formed cap 240 which surrounds sealing portion 238. Sealing portion 238 contacts a valve seat 242 on valve body 216. A coil spring 244 acts on cap 240 to maintain valve 226 in a sealed condition against valve seat 242. The other end of coil spring 244 presses against a valve end cap 246, which is secured to valve body 216 with a threaded joint 248.

Valve end cap 246 includes a puncture pin 250 which is operable to pierce a frangible seal on the end of a gas-charge bearing cylinder 252. Cylinder 252 is received in pressure chamber 204 and is removable therefrom by virtue of a housing cap 254 which is threadably received on housing 200. Cap 254 may be used to force cylinder 252 over pin 250 to release the gas charge from the cylinder. Alternately, a screw device, as disclosed in U.S. Pat. No. 4,790,824, issued Dec. 13, 1988, may be used.

Valve end cap 246 includes an O-ring 256 which provides a seal about a neck 252a of cylinder 252 to form a gastight seal thereabout. Valve assembly 214 is maintained in place in housing 200 by transfer tube 224 on one side of the assembly and by a split ring 258 which is located on the other side of the valve assembly.

An actuator mechanism 260 is operable to open poppet valve 226, thereby delivering a gas charge from cylinder 252 through the valve assembly into ampule-receiving chamber 202. Mechanism 260 includes a rocker-arm support 262 which is fixed on one side of valve body 216 and provides a pivoting support for a rocker arm 264. One end of the rocker arm is pivotably mounted on rocker-arm support 262 while the other end extends through a slot 266 in the side of housing 200. An actuator lever 268 is mounted on the free end of rocker arm 264 and extends along the exterior of housing 200. Assembly 260 is constructed such that when lever 268 is shifted toward housing 200, into a firing position, rocker arm 264 acts on poppet valve shaft 230, thereby opening poppet valve 226 and allowing passage of a gas charge from cylinder 252 into ampule-receiving chamber 202. Movement of gas into chamber 202 causes an ampule plunger-driving piston 270 to shift toward the free end of chamber 202, thereby acting on an ampule plunger received in the chamber. Piston 270, in the preferred embodiment, is a cylindrical, cap-like structure which includes a groove 272 about the periphery thereof and includes an O-ring 274 received in the groove.

Piston 270 is normally biased toward one end of chamber 202 by a spring 276. Spring 276 is of sufficient strength to return piston 270 to its ready position at the end of the chamber but does not provide sufficient resistance to decrease the force of piston 270 when a gas charge is caused to act upon it.

An injection-counting ring 278 is received in a groove 280 formed about housing 200 adjacent valve assembly 214. Referring now specifically to FIG. 5, ring 278 has alternating deep, or injection allowing, 282 and shallow, or injection prohibiting, 284 notches spaced evenly about the periphery thereof. The ring is constructed and arranged such that actuator lever 268 may not be moved to the firing position when received in a shallow notch 284 and may be moved to the firing position when received in a deep notch 282. A set screw 286 is received in ring 278 and includes a spring-biased dog 288 which acts with a series of detents 290 arranged about the periphery of groove 280. Dog 288 and detents 290 are constructed such that ring 278 may be rotated in only one direction about housing 200. A series of numbers, indicative of the number of injections which may be powered by a single cartridge, is provided about the periphery of ring 278.

In the example shown in the preferred embodiment, cartridge 252 contains a gas charge which is sufficient to provide five injections of medication carried in ampules, such as ampule 12. In this particular instance, ampule 12 contains 1.0 cc of medication. The patient using the assembly is taught to rotate ring 278 following each injection to a position where actuator lever 268 is received in a shallow notch. The ring must then be moved to a deep notch before the device may be used again. Appropriate notations are provided to indicate that a new cylinder must be inserted in pressure chamber 204 after a fifth injection is provided.

To use assembly 10 to administer an injection, device 14 is initially prepared by rotating ring 278 to a zero position with actuator lever 268 received in a shallow notch. A fresh cylinder 252 is installed in the recess in valve end cap 246 and housing cap 254 is installed and tightened on the housing. The action of tightening housing cap 254 causes a frangible seal in neck 252a of cylinder 252 to be punctured by puncture pin 250, thereby releasing a part of the gas charge in the cylinder into the first stage of the valve assembly.

An ampule 12 containing the desired amount of medication is prepared as previously described. Fill adaptor 63 and needle assembly 70 are removed. An ampule sleeve 80 is installed over the ampule body and the ampule installed on device 14 with plunger head 45 in contact with driving piston 270. Sleeve 80 and adaptor 63 may be sized to prevent installation of the ampule on device 14 with adaptor 63 and needle assembly 71 in place. The ampule and sleeve are secured to device 14 by means of the lug, or bayonet mount, which is provided by lugs 82 and grooves 78. Once the ampule and device are formed into the desired assembly, and ring 278 is rotated such that actuator lever 268 is over a deep groove, the assembly is brought into contact with the patient's skin, with the free end of end cap 46 contacting the skin. The actuator lever is then pressed, releasing a gas charge from the first stage of the valve assembly into the ampule-receiving chamber, thereby moving the piston toward the free end of the chamber and in turn, depressing plunger 32 forcing the medication through needle 60 with sufficient velocity to form a skin-piercing injection stream which will extend below the level of the outer layer of the patient's skin to a desired depth.

Once the injection has been administered, ring 278 is rotated to a position such that a shallow notch is aligned with actuator lever 268 to prevent inadvertent firing of device 14. The ampule and sleeve are removed from the device. The ampule may be discarded, or may be sterilized and reused. Device 14 and sleeve 80 are then ready for the next injection.

Once poppet valve 226 is allowed to close, by release of actuator lever 268 and rocker arm 264, the gas charge will bleed out of chamber 202 around plug 212 and spring 276 will act on piston 270 to return the piston to its ready position at the interior end ampule-receiving chamber 202. Although a preferred embodiment of the assembly of the invention has been disclosed, it should be appreciated that variations and modifications may be made thereto without departing from the scope of the invention as defined in the appended claims.

It is claimed and desired to secure as letters patent:

1. A hypodermic syringe comprising:
    an ampule body having a plunger end and an orifice end, said body having a generally elongate cylindrical form with an outer wall of predetermined diameter and an inner wall defining a medication retaining cavity, a flange which is a continuation of said inner wall which is located at said orifice end and extends axially outward therefrom, said flange having an outer wall which is located intermediate said body inner wall and said body outer wall;
    an elongate plunger, one end thereof having a seal-carrying groove formed about the periphery thereof and being received in said medication retaining cavity with a seal received in said groove;
    an orifice-bearing end cap fixed to said orifice end, said end cap having a generally cylindrical form including a medication-receiving portion extending axially into said medication retaining cavity at one end thereof, said end cap having a groove extending about said medication-receiving portion at the base thereof, said groove being conformal with said flange on said body;
    a truncated hypodermic needle received in said end cap and having a channel extending therethrough, said channel communicating with the narrower end of said bore;
    a filling needle having connecting means thereon; and
    a removable external fill adaptor having a receptacle on one end thereof for receiving said end cap therein and a bore extending therethrough, said bore being aligned with said truncated hypodermic needle on said end cap, means on the other end of said adaptor cooperating with said connecting means for securing said filling needle to said adaptor.

2. The hypodermic syringe of claim 1 wherein said filling needle is a conventional hypodermic needle and said connecting means includes a luer lock fitting.

3. The hypodermic syringe of claim 1 wherein said truncated hypodermic needle is co-terminal with the other end of said end cap.

4. The hypodermic syringe of claim 1 wherein said fill adaptor is constructed and arranged to be removed from the syringe when the syringe is used with a powered, non-invasive hypodermic injection device and to be retained on the syringe when the syringe is used to provide an invasive injection.

5. The hypodermic syringe of claim 1 wherein the syringe is used with a non-invasive hypodermic injection device and includes attachment means for securing the syringe to the device, said attachment means including an elongate ampule sleeve which extends about said ampule body along the length thereof, one end of said sleeve being located adjacent said plunger end of said body, the other end of said sleeve being located adjacent the orifice end of said body, said attachment means being constructed and arranged to grasp said end cap.

6. The assembly of claim 5 wherein said sleeve has lugs spaced about the periphery of one end thereof.

7. The assembly of claim 6 wherein said ampule body has medication-volume indicia thereon and said sleeve has at least one wasted area along a portion thereof for providing a viewing window for said indicia.

8. A patient-fillable ampule and a non-invasive hypodermic injection device assembly comprising:
    an injection device including a housing having an ampule-receiving chamber, a gas charge, and means for delivering a predetermined amount of gas to said ampule-receiving chamber; and
    a patient-fillable ampule therefore comprising:
    an ampule body having a plunger end and an orifice end, said body having a generally elongate cylindrical form with an outer wall of predetermined diameter and an inner wall defining a medication retaining cavity, a flange which is a continuation of said inner wall which is located at said orifice end and extends axially outward therefrom, said flange having an outer wall which is located intermediate said body inner wall and said body outer wall;
    an elongate plunger, one end thereof having a seal-carrying groove formed about the periphery thereof and being received in said medication retaining cavity with a seal received in said groove and the other end thereof formed into a broadened head;
    an orifice-bearing end cap fixed to said orifice end, said end cap having a generally cylindrical form of substantially the same outside diameter as said outer wall predetermined, larger diameter along a first length thereof and a stepped-down, smaller diameter along a second length thereof, said end cap including a medication-receiving portion extending axially from the larger diameter end thereof into said medication retaining cavity, said medication receiving portion having a truncated conical bore therein with the wider end of said bore located in said medication retaining cavity, said end cap having a groove extending about said medication receiving portion at the base of said medication receiving portion, said groove being conformal with said flange on said body;

a truncated hypodermic needle received in said end cap at the smaller diameter end thereof and having a channel extending therethrough, said channel communicating with the narrower end of said bore; and attachment means including an elongate ampule sleeve for attaching said ampule to said device which extends about said ampule body along the length thereof, one end of said sleeve being located adjacent said plunger end of said body, the other end of said sleeve being located adjacent said orifice end and being constructed and arranged to grasp said end cap about said stepped-down diameter.

9. The assembly of claim 8 wherein said truncated hypodermic needle is co-terminal with the smaller diameter end of said end cap and which further includes a filling needle having connecting means thereon and a removable, external fill adaptor having a receptacle on one end thereof for receiving said end cap therein, a bore extending therethrough, said bore being aligned with said truncated hypodermic needle on said end cap and means on the other end of said adaptor cooperating with said connecting means for securing said filling needle to said fill adaptor.

10. The hypodermic syringe of claim 9 wherein said filling needle is a conventional hypodermic needle and said connecting means includes a luer lock fitting.

11. The hypodermic syringe of claim 9 wherein said fill adaptor is constructed and arranged to be removed from the syringe when the syringe is used with a powered, non-invasive hypodermic injection device and to be retained on the syringe when the syringe is used to provide an invasive injection.

12. The assembly of claim 8 wherein said ampule body has medication-volume indicia thereon and said sleeve has at least one wasted area along a portion thereof for providing a viewing window for said indicia.

13. The assembly of claim 8 wherein said device includes a retainer collar located at an end of said housing for retaining said sleeve and said ampule on said housing, said sleeve having lugs spaced about the periphery of one end thereof and said collar having lug-receiving grooves therein.

14. The assembly of claim 8 wherein said device includes
an elongate, hollow housing having said ampule-receiving chamber at one end thereof, a pressure chamber at the other end thereof and a partition located between said chambers, said partition having a gas-delivery passage extending therethrough;
said pressure chamber having said gas charge and a valve assembly therein, said valve assembly including:
a valve body having a cavity therein, said cavity including a valve-shaft receiving portion extending from one side of said body to the other side thereof and a gas-passage portion;
a valve end cap secured to the other side of said body having a recess for receiving an end of a gas-charge containing cartridge and a puncture pin located in said recess for piercing said cartridge received in said pressure chamber to release said gas charge;
a poppet valve having a valve head for closing the cavity on the other side of said valve body, a valve shaft received in said cavity and extending therethrough to said one side of said valve body;
a rocker-arm support fixed to said one side of said valve body, a rocker arm pivotably secured at one end thereof to said rocker-arm support with the other, free end, of said rocker arm extending through a slot in the side of said housing to the exterior thereof, and an elongate actuator lever secured to the free end of said rocker arm and extending along the exterior of said housing, said rocker arm and said rocker-arm support being constructed and arranged to provide shiftable contact between said poppet valve shaft and said rocker arm to shift said poppet valve to an open position with movement of said lever towards said housing;
a gas transfer tube extending between said gas-delivery passage and said valve body cavity for directing a gas charge to said ampule-receiving chamber when said poppet valve is opened;
an ampule plunger-driving piston shiftably located in said ampule-receiving chamber; and
an ampule retaining collar located on said one end of said housing for securing an ampule to said housing, said collar having ampule sleeve bayonet-receiving grooves therein for receiving a bayonet lug on an ampule sleeve.

15. The assembly of claim 14 which further includes an injection-counting ring received in a groove extending about said housing, said ring having alternating injection allowing/preventing notches formed about the periphery thereof and including means to allow one-way only rotation of said ring relative to said housing.

* * * * *